United States Patent [19]

Lundquist

[11] 4,105,027

[45] Aug. 8, 1978

[54] INHALATION DEVICE

[75] Inventor: Ingemar H. Lundquist, Oakland, Calif.

[73] Assignee: Syntex Puerto Rico, Inc., Humacao, P.R.

[21] Appl. No.: 735,663

[22] Filed: Oct. 26, 1976

Related U.S. Application Data

[63] Continuation of Ser. No. 586,771, Jun. 13, 1975, abandoned.

[51] Int. Cl.² ............................................ A61M 15/08
[52] U.S. Cl. .................................... 128/206; 128/266; 128/208
[58] Field of Search ................ 128/266, 265, 206–209, 128/210, 198–201, 272; 131/170 A, 10.1; 401/134, 135

[56] References Cited

U.S. PATENT DOCUMENTS

| 1,406,903 | 2/1922 | Rose | 128/265 |
| 1,406,904 | 2/1922 | Rose | 128/266 |
| 2,549,303 | 4/1951 | Friden | 128/206 |
| 3,885,607 | 5/1975 | Peltier | 128/272 |
| 3,906,950 | 9/1975 | Cocozza | 128/206 |

FOREIGN PATENT DOCUMENTS

| 149,094 | 11/1952 | Australia | 128/198 |
| 627,662 | 8/1949 | United Kingdom | 128/206 |

Primary Examiner—Stephen C. Pellegrino
Assistant Examiner—Henry J. Recla
Attorney, Agent, or Firm—Tom M. Moran; Joseph I. Hirsch

[57] ABSTRACT

An inhalation device having an elongate housing having a passageway for the movement of air therethrough. The passageway terminates in an emptying chamber adjacent that end of the housing which is adapted for insertion into the mouth or nasal passages of a user thereof. The housing has means for receiving and opening a container holding a unit dose of powdered medicament for administration. The opening means includes first means for placing the interior of the opened capsule in communication with the atmosphere and second means for placing the interior of the opened capsule in communication with the emptying chamber via the passageway in the housing. During inhalation, air drawn through the first means causes the powdered medicament to be expelled from the container through the second means, the passageway and the emptying chamber into the nose, throat or lungs of the user where beneficial or therapeutic action of the medicament occurs.

10 Claims, 8 Drawing Figures

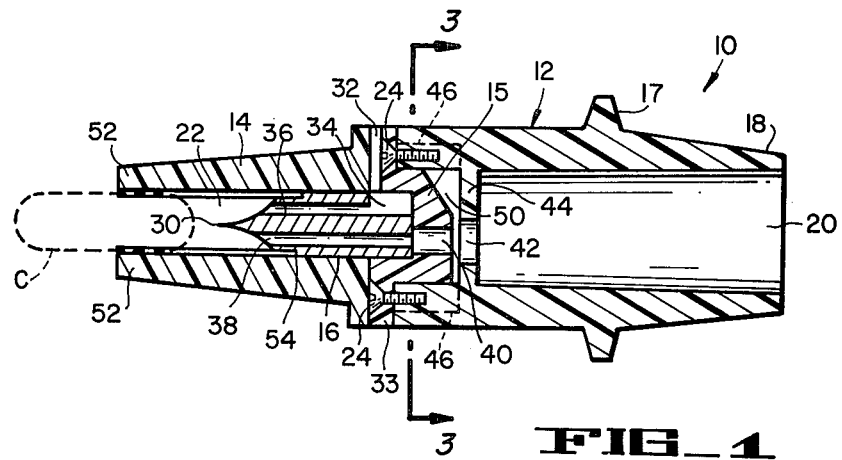
FIG_1
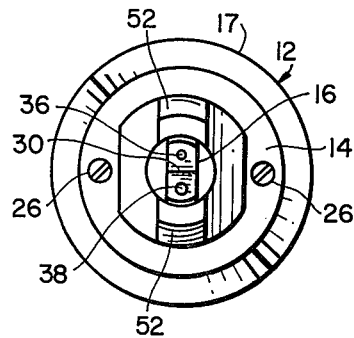
FIG_2
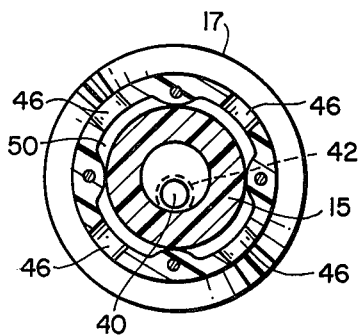
FIG_3

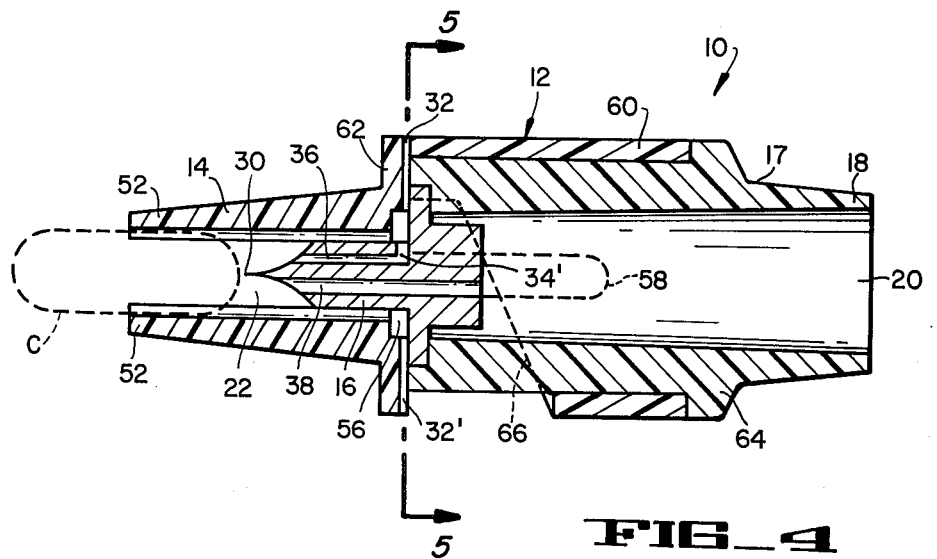
FIG_4
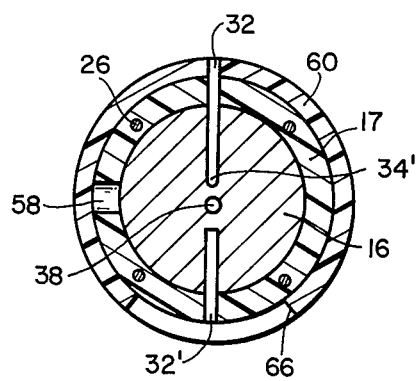
FIG_5

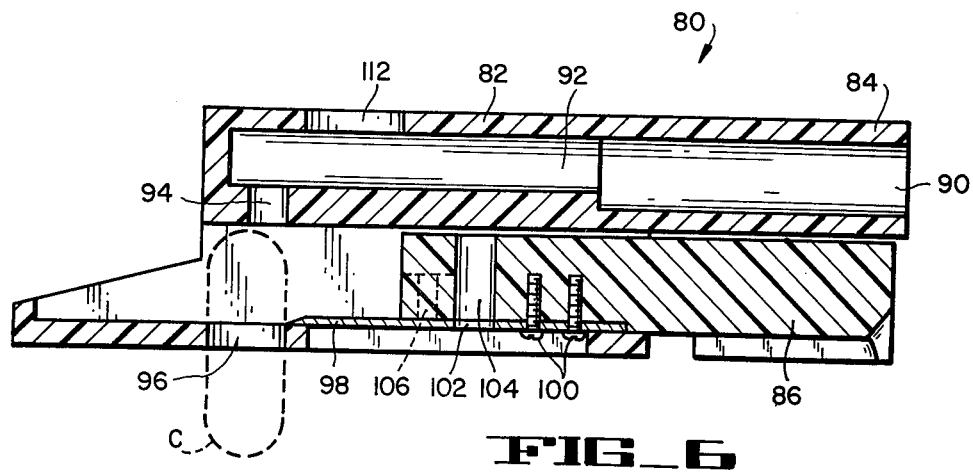
FIG_6
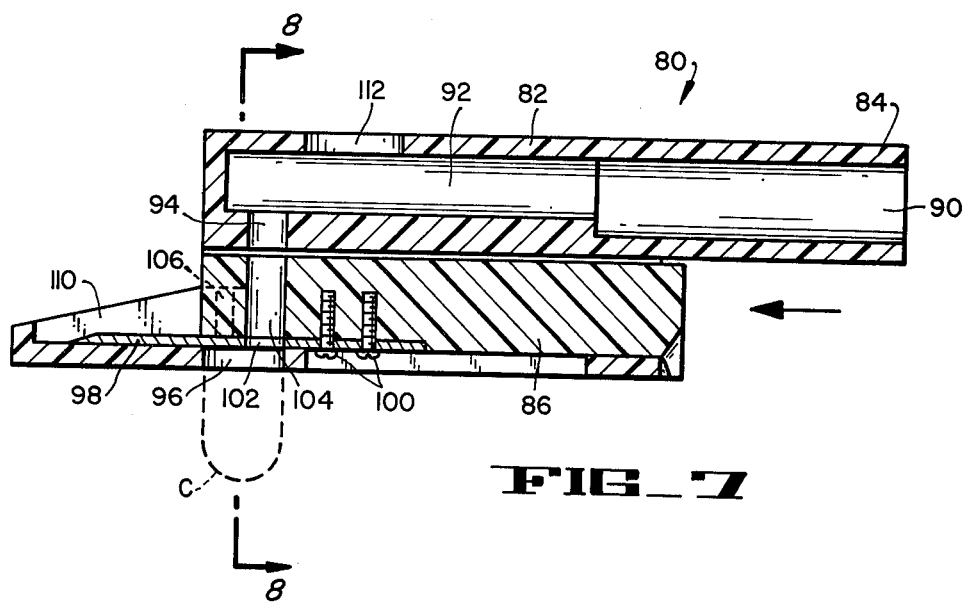
FIG_7
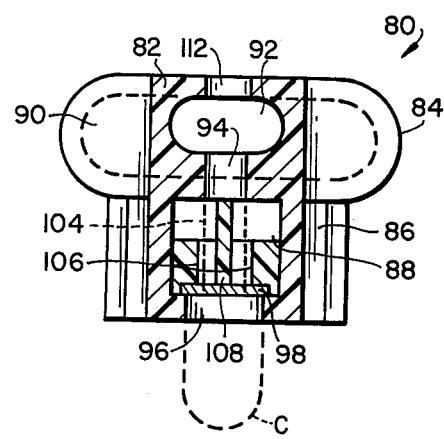
FIG_8

INHALATION DEVICE

This is a continuation, of application Ser. No. 586,771 filed June 13, 1975 now abandoned.

FIELD OF THE INVENTION

This invention is related to devices for the administration of powdered medicaments by inhalation. More particularly, this invention relates to an inhalation device which is capable of causing a powdered medicament, held within a container inserted into the device, to be rapidly and effectively dispensed from the container, entrained in the air stream being inhaled and, thusly, carried into the nose, throat or lungs of the user where beneficial or therapeutic action of the medicament occurs.

BACKGROUND OF THE INVENTION

Known, prior art inhalation devices include, for example, those shown in U.S. Pat. Nos. 988,352; 2,507,702; and 2,603,216; and Great Britain Pat. No. 1,118,431.

SUMMARY OF THE INVENTION

The inhalation devices of the present invention include an elongate housing having a passageway for the movement of air therethrough, one end of the housing being adapted for insertion into the mouth or nasal passages of a user thereof. The passageway terminates in an emptying chamber adjacent the output end of the housing. The housing includes means for receiving and opening a container holding a unit dose of powdered medicament for administration by inhalation. The opening means includes first means for placing the interior of the opened container into communication with the atmosphere and second means for placing the interior of the opened container in communication with the emptying chamber via the passageway in the elongate housing.

In a first embodiment, the opening means comprises a pointed piercing member against which the capsule is pushed during the manual insertion thereof into the container receiving means. Passageways extending through the pointed piercing means connect the interior of the container with the atomosphere and the emptying chamber (via the passageway in the housing), respectively.

In a second embodiment, the closed container is manually inserted into a port in the housing. Thereafter, a cutting member, slideable within a guide channel in the lower portion of the housing, and carrying a sharp cutting blade is manually moved from a first, retracted position to a second, container-severing position. In the second position, the slideable member includes first and second means for placing the interior of the now-opened container in communication with the atmosphere and the emptying chamber (via the passageway in the housing), respectively.

The devices of this invention also include one or more ports or openings in the housing through which air is drawn during inhalation. These ports or openings provide additional air flow in which the powdered medicament is entrained after it has been expelled from the container. Optionally, means to vary the size of the ports or openings can be provided to vary the amount of air drawn therethrough. In this manner, the patient can control, to a certain extent, the rate of air flow drawn through the container during inhalation. This, in turn, enables the patient to control, within limits, the delivery characteristics (speed of delivery, number of inhalations, etc.) which can be obtained with the devices of this invention.

As noted above, the devices of this invention have means associated therewith for automatically opening the container as it is inserted into the device or means to open the container after it has been inserted into the device. Such means eliminate the need to manually open the container prior to insertion, and, thusly, reduce the possibility of inadvertent spillage of the medicament prior to inhalation.

It has been found that, with the inhalation devices of this invention, the powdered medicament held within the container is rapidly and efficiently entrained in the airstream passing through the device during inhalation and, as such, can be carried into the nose, throat or lungs of the user thereof for beneficial or therapeutic action of the medicament to occur.

container, as used herein, is intended to include any means by which a unit dose of medicament is presented to the device for administration. Capsules, such as gelatin capsules, are the presently preferred form of containers; however, it is contemplated that other forms would be equally suitable if appropriate structural modifications of the device, to accommodate the different carriers, are made as, and if, necessary.

BRIEF DESCRIPTION OF THE DRAWINGS

The foregoing and still further features and advantages of the invention will become more apparent from the following detailed description, taken together with the accompanying drawings wherein:

FIG. 1 is a vertical cross-sectional view of one embodiment of an inhalation device of the present invention;

FIG. 2 is an end view of the left-hand side of the inhalation device of FIG. 1;

FIG. 3 is a cross-sectional view of the inhalation device of FIG. 1 taken along line 3—3 of FIG. 1;

FIG. 4 is a vertical cross-sectional view of an alternate embodiment of the inhalation device of the present invention;

FIG. 5 is a cross-sectional view of the inhalation device of FIG. 4 taken along line 5—5 of FIG. 4;

FIG. 6 is a vertical cross-sectional view of a further alternate embodiment of an inhalation device of the present invention, showing the capsule opening means in the retracted position;

FIG. 7 is a further vertical cross-sectional view of the device of FIG. 6 showin the capsule opening means in the closed position after a capsule inserted into the device has been opened; and FIG. 8 is a cross-sectional view of the inhalation device of FIGS. 6 and 7 taken along line 8—8 of FIG. 7.

Referring to FIG. 1, there is shown an inhalation device 10 having a housing 12 comprising a front end member 14, an intermediate member 15 which supports capsule opening means 16, and a rear end member 17 terminating in a mouthpiece 18. Mouthpiece 18 can be redesigned to permit insertion into the nasal passages or, if desired, an adapter (not shown) can be placed over the mouthpiece to permit nasal use. Inside mouthpiece 18 is an emptying chamber 20 connected, in the manner described below, to entrance chamber 22 at the end of front end member 14 which is adapted to receive capsule C containing the medicament intended to be dispensed through utilization of this device. Capsule opening means 16, one end of which extends toward emptying chamber 20 and the other end of which partially extends into entrance chamber 22, is securely held in position by screws 24. Other screws 26 (see FIG. 2) are used to hold members 14, 15 and 17 securely together. The end of capsule opening means 16 which extends into entrance chamber 22 terminates at a sharp point 30 against which capsule C is pushed as it is being inserted into chamber 22. Passageway 32 in the upper portion of flange 33 encircling intermediate member 15 is in communication with chamber 22 by means of a notch 34 and passageway 36 extending through capsule opening means 16. Passageway 38 extending longitudinally through capsule opening means 16 provides communication between entrance chamber 22 and emptying chamber 20 via port 40 in intermediate member 15 and opening 42 in flange 44 forming one end of chamber 20. Flange 44 with opening 42 can be eliminated if desired, whereby port 40 will communicate directly with emptying chamber 20. Ports 46 (see FIG. 3) in that portion of member 17 adjacent intermediate member 15 also communicate with emptying chamber 20 via space 50 and opening 42.

In use, the medicament-containing capsule C is inserted between arcuate arms 52 of front end member 14 and pushed against capsule opening means 16 until the leading edge of the capsule contacts stop 54. When the capsule is in position against stop 54, it is closed to the atmosphere except for the communication via passageways 36 and 38 through opening means 16. The patient then inhales through mouthpiece 18 whereupon air flowing through passageway 32, notch 34 and passageway 36 causes the powdered medicament in capsule to be expelled through passageway 38, port 40 and opening 42 into emptying chamber 20. The powdered medicament, now dispensed from the capsule, is entrained in the air stream flowing through emptying chamber 20 which includes that air drawn into chamber 20 via ports 46. In this manner, the medicament is carried through the mouth and into the throat or lungs of the user where beneficial or therapeutic action of the medicament occurs.

In the device of FIGS. 4 and 5, like numerals are utilized to represent like elements of the device of FIGS. 1-3, although the configuration thereof may be different in certain respects. The device of FIGS. 4 and 5 is similar to the device of FIGS. 1-3; however, intermediate member 15 and flange 44 with opening 42 are eliminated, passageway 32 is in communication with passageway 36 via hole 34' in one side of the interior end of capsule opening means 16, and, in addition, there is a further passageway 32', directly opposite passageway 32, which communicates with hole 34' and passageway 36 via hollow annular ring 56 which encircles capsule opening means 16 in the interior end of front end member 14. Instead of ports 46, rear end member 17 has, through one surface thereof, a port 58 which underlies substantially cylindrical rotatable member 60 adapted for rotational movement about the interior end of member 17. Member 60 is maintained in place by flange 62 on member 14 and flange 64 on member 17. A portion of the cylindrical surface is cut-away to define a slanting or diagonal surface 66 whereby, as member 60 is rotated, more or less (depending upon the degree and manner of rotation) of underlying port 58 is exposed. This, in turn, permits the patient to control, to a certain extent, the amount of air which is drawn through the capsule during inhalation. That is, by rotation of member 60 to the position where port 58 is completely closed, all air drawn through the device (and thus inhaled) will pass through the capsule. For a given patient (with a given lung capacity) and a given powder formulation, the medicament will be dispensed with the least amount of effort or in the least amount of time, relative to other positions of rotatable member 60. With member 60 rotated to the position as shown in FIGS. 4 and 5 where a portion of port 58 is open, air, during inhalation, will also be drawn the capsule. This will result in slower emptying of the capsule contents. With member 60 rotated to the position where port 58 is completely open, even more air will be drawn through port 58 and, accordingly, less air will be drawn through the capsule. This will result in even slower emptying of the capsule contents. This device is used in the same manner as the device of FIGS. 1-3, with the exception that the patient can control, to a certain extent as by rotation of member 60, the manner (speed, number of inhalations, etc.) of medicament delivery.

Referring to FIGS. 6–8, there is shown an inhalation device 80 having a housing comprising a capsule receiving member 82 terminating in a mouthpiece 84, and a capsule cutting member 86 which is slideable within guide channel 88 (see FIG. 8) in the lower portion of member 82. Adjacent mouthpiece 84 is an emptying chamber 90 which is connected via passageways 92 and 94 to that end of the device remote from the mouthpiece. Port 96, beneath passageway 94, is adapted to receive a medicament-holding capsule C. Slideable cutting member 86 has a sharp cutting blade 98, for example a metal blade, secured to the main body thereof by means of screws 100. Hole 102 in blade 98 and passageway 104 in the main body of member 86 are in alignment with passageway 94 and port 96 when cutting member 86 is in the position shown in FIG. 7, whereby the capsule and the contents therein are in communication with emptying chamber 90 adjacent mouthpiece 84 after the capsule is opened. Capsule C is also open to the atmosphere by means of passageways 106 on opposite sides of divider 108.

In use, with cutting member 86 in the position as shown in FIG. 6, the patient manually inserts a medicament-holding capsule into port 96, then manually pushes cutting member 86 to the position shown in FIG. 7. This operation severs the top of the capsule which is ejected through opening 110. After the capsule top has been severed, the capsule is closed to the atmosphere except for communication via passageways 106 and 108 through cutting member 86. The patient then inhales through the mouthpiece whereupon air drawn through passageways 106 into the capsule causes the powder medicament to be expelled through hole 102 in cutting blade 98, passageways 104, 94 and 92 into emptying chamber 90. The powdered medicament, now dispensed from the capsule, is entrained in the air stream flowing through emptying chamber 90, which includes air drawn into chamber 90 via port 112 in the top of passageway 92. If desired, the patient can place his or her finger over all or a portion of port 112 to affect, to a certain extent, the delivery characteristics of this device, as described above with reference to the device of FIGS. 4-5.

Passageways, holes, and/or chambers as shown in these devices can be squared-off or streamlined, as desired, as long as the particular configuration selected is effective to cause the powdered medicament to be expelled from the capsule, in the desired number of inhalations, during the inhalation, medicament-administering process.

The entire device can be made of metal but preferably is made of suitable plastic material, such as nylon, polyacetal or polypropylene. The capsule opening means 16 of FIGS. 1-5 and the cutting blade of FIGS. 6-8 are preferably made of metal to permit a greater number of capsule openings before sharpening or replacement is necessary.

The physical properties of each medicament formulation (i.e., the ability to fluidize and the flow characteristics thereof) will affect the ease or manner in which it is dispensed with these or other inhalation devices. However, for a given powdered formulation, varying the dimensions of the various passageways, the number, positioning and size of the ports in the housing, and/or, in general, modification of the overall internal configuration and shape of the various elemental parts thereof, devices can be designed to deliver the medicament in a different number of inhalations or in a longer or shorter period of time, depending upon the nasal or lung capacities and strengths of each particular user. Quite obviously, no single device will be optimal for all persons requiring administration of powdered medicaments since, for example, people with differing lung capacities are known to generate flow rates from about 30 liters/minutes or so to about 120 liters/minutes or so through inhalation devices of this and known types. Nonetheless, the devices of this invention afford such variability, through proper selection of the various design parameters listed above, that a device, embraced within the scope of this invention, can be designed for a particular patient generated flow rate to deliver the medicament according to a set of pre-determined objectives (e.g., slow or fast administration, one or many inhalations, etc.). The net result is that a family of devices, all embraced within the scope of the present invention, can be designed, each of which will deliver the medicament under a different, given set of selected administration conditions. Conversely, the devices of this invention can be designed to cover an extensive range of operating conditions, and thus be made suitable for use by a variety of persons having differing inhalation abilities or capacities.

While the present invention has been described with reference to specific embodiments thereof, it will be understood by those skilled in this art that various changes may be made and equivalents may be substituted without departing from the true spirit and scope of the invention. For example in the device of FIGS. 6-8, port 96 can be placed closer to mouthpiece 90 and slideable member can be made to move toward the user (i.e., from left to right) to open the capsule, in which case the medicament expelled from the capsule will have less distance to travel before it exits from the device. Additionally, other modifications, as would be obvious to those skilled in this art, in view of this disclosure, may be made to adapt a particular sitation, material or composition of matter, structural desirability, or then-present objective to the spirit of this invention without departing from its essential teachings.

What is claimed is:

1. A breath-actuated inhalation device for dispensing a medicament from a medicament-holding, cylindrical capsule having closed hemispherical ends, said device comprising an elongate housing having a passageway for the movement of air therethrough, said housing having a first end and a second end, one of said ends being an output end adapted for insertion into the mouth or nasal passages of a user thereof, said passageway terminating in an emptying chamber adjacent the output end of said housing;

means for receiving a closed, medicament-holding, cylindrical capsule having closed hemispherical ends directly from the exterior of said device, said medicament-receiving means including sharply pointed piercing means to penetrate one hemispherical end of the capsule as the capsule is manually pushed thereagainst, first, communication means comprising a first passageway extending through and within said piercing means for placing the interior of the container in communication with the atmosphere surrounding said device, and second communication means comprising at least one additional passageway extending through and within said piercing means for placing the interior of the container in communication with said emptying chamber, said first and second communication means communicating with the interior of the capsule through openings near the point of said pointed piercing means, the capsule being otherwise closed to the atmosphere when said first and second communication means are in communication with the interior thereof;

whereupon, during inhalation with said piercing means penetrating the capsule, air drawn through said first communication means causes the powdered medicament to be expelled from the medicament-holding capsule through said second communication means and said emptying chamber into the nose, throat or lungs of a user thereof.

2. The device of claim 1 further including at least one opening in said housing adjacent the outlet side of said second communication means through which air can be drawn during inhalation.

3. The device of claim 1 further including an opening in said housing through which air can be drawn during inhalation, and means adjacent said opening for varying the effective size of said opening.

4. The device of claim 1 further including an opening in said housing through which air can be drawn during inhalation and rotatable means adjacent said opening for completely closing said opening or varying the effective size of said opening upon rotation thereof.

5. The device of claim 1 wherein said pointed piercing means is adjacent the end of said housing remote from said output end, said pointed piercing means extending away from said output end in a direction along the longitudinal dimension of said housing.

6. The device of claim 1 wherein said first and second communication means communicate with the container through closely adjacent, non-opposed portions thereof.

7. A breath-actuated inhalation device for dispensing a medicament from a medicament-holding, cylindrical capsule having closed hemispherical ends, said device comprising an elongate housing having a passageway for the movement of air therethrough, said housing having a first end and a second end, one of said ends being an output end adapted for insertion into the mouth or nasal passages of a user thereof, said passageway terminating in an emptying chamber adjacent the output end of said housing; a first opening in said housing; means for receiving a closed medicament-holding, cylindrical capsule having closed hemispherical ends directly from the exterior of said device, said medicament-receiving means including sharply pointed piercing means to penetrate one hemispherical end of the capsule as the capsule is manually pushed thereagainst, first communication means comprising a first passageway extending through and within said piercing means for placing the interior of the capsule in communication with the atmosphere surrounding said device via said opening in said housing, and second communication means comprising at least one additional passageway extending through and within said piercing means for placing the interior of the capsule in communication with said emptying chamber, the capsule being otherwise closed to the atmosphere when said first and second communication means are in communication with the interior thereof; said pointed piercing means being adjacent the end of said housing remote from said output end and extending away from said output end in a direction along the longitudinal dimension of said housing; a second opening in said housing adjacent the outlet side of said second communication means through which air can be drawn during inhalation whereupon, during inhalation with said piercing means penetrating the capsule, air drawn through said first communication means causes the powdered medicament in the medicament-holding capsule to be expelled therefrom through said second communication means and said emptying chamber into the nose, throat or lungs of a user thereof.

8. The device of claim 7 further including means adjacent said second opening for varying the effective size thereof.

9. The device of claim 7 further including rotatable means adjacent said second opening for completely closing said second opening or varying the effective size thereof upon rotation of said rotatable means.

10. The device of claim 7 wherein said first and second communication means communicate with the container through openings near the point of said pointed piercing means.

* * * * *